United States Patent
Xu et al.

(10) Patent No.: US 10,125,119 B2
(45) Date of Patent: Nov. 13, 2018

(54) SERIES OF RESVERATROL-DERIVATIVE FLUORESCENTLY LABELED MOLECULES AND SYNTHESIS METHOD THEREOF

(71) Applicant: Hangzhou Normal University, Hangzhou (CN)

(72) Inventors: Weiming Xu, Hangzhou (CN); Pengfei Zhang, Hangzhou (CN); Wanmei Li, Hangzhou (CN); Kui Du, Hangzhou (CN); Kejie Chai, Hangzhou (CN)

(73) Assignee: Hangzhou Normal University, Hangzhou (CN)

( * ) Notice: Subject to any disclaimer, the term of this patent is extended or adjusted under 35 U.S.C. 154(b) by 0 days.

(21) Appl. No.: 15/914,997

(22) Filed: Mar. 7, 2018

(65) Prior Publication Data

US 2018/0273514 A1    Sep. 27, 2018

(30) Foreign Application Priority Data

Mar. 22, 2017 (CN) .......................... 2017 1 0174937

(51) Int. Cl.
  *C07D 403/04* (2006.01)
  *C07D 403/14* (2006.01)
  *C09K 11/06* (2006.01)

(52) U.S. Cl.
  CPC ............ *C07D 403/04* (2013.01); *C09K 11/06* (2013.01); *C09K 2211/1044* (2013.01); *C09K 2211/1059* (2013.01)

(58) Field of Classification Search
  CPC .... C07D 403/04; C07D 403/14; C09K 11/06; C09K 2211/1044; C09K 2211/1059
  See application file for complete search history.

(56) References Cited

FOREIGN PATENT DOCUMENTS

CN    102688493 A    9/2012

OTHER PUBLICATIONS

Jian Wang et al., Ethynyl-Capped Hyperbranched conjugated Polytriazole: Click Polymerization, Clickable Modification, and Aggregation-Enhanced Emission. <Macromolecules>. 2012, 45:7692-7703.
Wenhui Dong et al., Anionic conjugated polytriazole: direct preparation, aggregation-enhanced emission, and highly efficient Al3+ sensing. <Polym. Chem.>. 2016, 7:5835-3839.
Chao Shen et al., Desgin and Synthesis of Carbohydrate-derived Fluorescent Probes and their Application in Cell Imaging<Chinese Chemistry Association 29th Annual Meeting Abstracts-07 subcommittee: organic chemistry>. 2014.

*Primary Examiner* — Alexander R Pagano
*Assistant Examiner* — Ebenezer O Sackey
(74) *Attorney, Agent, or Firm* — Zhihua Han

(57) ABSTRACT

The invention discloses a series of resveratrol-derivative fluorescently labeled molecules and a synthesis method thereof. The fluorescently labeled molecules has a molecular formula as shown in formula (I). The synthesis method includes the steps of adding a certain amount of resveratrol derivative and solvent in a reaction vessel, adding a fluorescent marker as shown in formula (III) and a certain amount of alkali, reacting at 20° C.-60° C. for 2-10 hours, and after the reaction is completed, spin-drying the reaction solvent and performing post-processing to obtain the products.

10 Claims, 1 Drawing Sheet

(a)           (b)           (c)

(a)           (b)           (c)

SERIES OF RESVERATROL-DERIVATIVE FLUORESCENTLY LABELED MOLECULES AND SYNTHESIS METHOD THEREOF

CROSS REFERENCE TO RELATED APPLICATION

This application claims the priority benefit of Chinese Patent Application No. 201710174937.4, filed on Mar. 22, 2017, which is hereby incorporated by reference in its entirety.

TECHNICAL FIELD

The present invention relates to the synthesis of a class of natural active molecule-derivatives, in particular to a series of resveratrol-derivative fluorescently labeled molecules and their synthesis.

BACKGROUND

The resveratrol series of compounds are polyphenols compounds, including resveratrol, pterostilbene, oxyresveratrol, piceatannol, combretastatin, erianin, and others. The resveratrol series of compounds exists naturally in grapes, mulberry, peanut and giant knotweed (*Polygonum cuspidatum*), and have demonstrated anti-oxidation and anti-free radical functions as their major characteristics. The resveratrol series of compounds are excellent natural antioxidants that can reduce blood viscosity, inhibit platelet aggregation and vasodilatation, maintain blood flow, prevent cancer incidence and progression, avert coronary heart disease, ischemic heart disease, and hyperlipidemia, delay aging, and prevent cancer. There is significant market demand for these compounds.

In the invention, the active series of resveratrol and resveratrol-derivatives are linked to a novel, low toxicity fluorescent maker, to synthesize a series of resveratrol-derivative fluorescently labeled molecules.

SUMMARY

One object of the present invention is to provide a resveratrol-derivative fluorescently labeled molecule with the core structure of 1,3,5-triazine represented by formula (I), in order to overcome the deficiencies of the prior art:

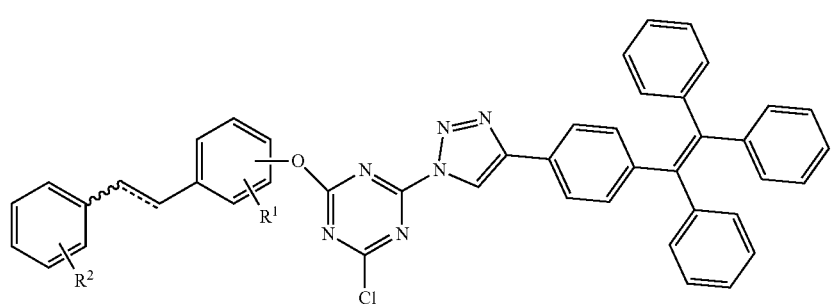

(I)

Wherein R1 is selected from the group consisting of hydrogen, hydroxyl, and methoxy, R2 is one or more of hydroxyl group and methoxy group, the R1-substituted benzene ring and the R2-substituted benzene ring are linked by a single or double bond, and the double bond can be cis or trans.

Another object of the present invention is to provide a method for preparing the above resveratrol-derivative fluorescently labeled molecules, by adopting the following technical solutions:

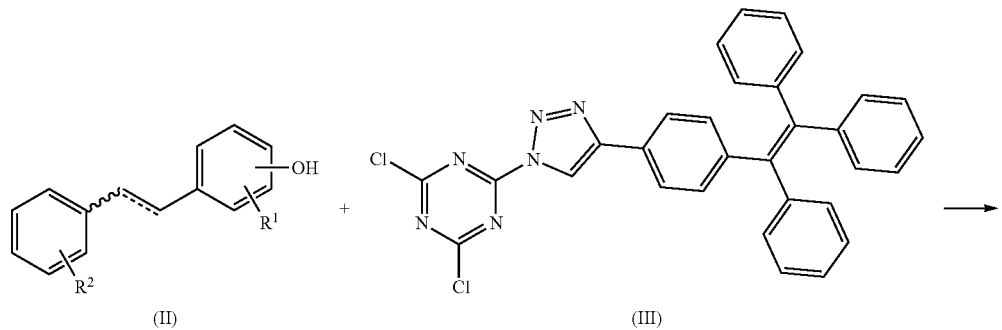

(II)     (III)

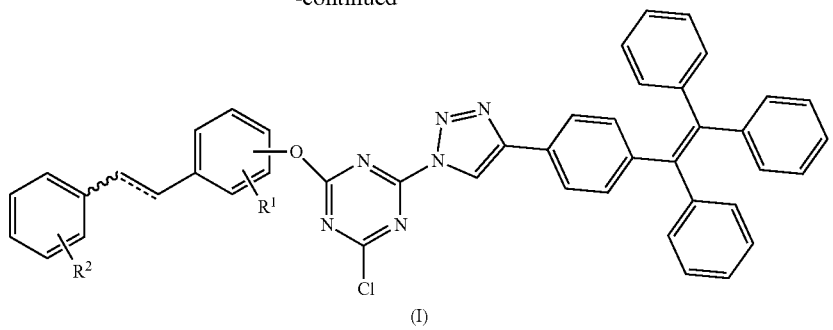

(I)

Adding a certain amount of resveratrol derivative and solvent in a reaction vessel, adding fluorescent marker as shown in formula (III) and a certain amount of alkali, reacting at 20-60° C. for 2-10 hours, and after the reaction is completed, spin-drying the reaction solvent, performing post-processing to obtain the products.

The resveratrol derivative used in the reaction can be selected from the group consisting of resveratrol, pterostilbene, oxyresveratrol, piceatannol, combretastatin, and erianin, and other molecules of formula (II).

The solvent used in the reaction is can be selected from the group consisting of methanol, ethanol, and acetone, preferably acetone. The molar ratio of the solvent to the resveratrol derivative is 5-10:1.

The alkali used in the reaction can be selected from the group consisting of sodium hydroxide, triethylamine, sodium carbonate, potassium carbonate, sodium bicarbonate, and potassium bicarbonate, preferably sodium carbonate. The molar ratio of the alkali to the resveratrol derivative is 1-2.5:1.

The fluorescently labeled molecule of formula (III) is 2,4-dichloro-6-[5-(4-trityl-phenyl)-[1,2,3] triazole-1-substitute)-[1,3,5] triazine. The molar ratio between the fluorescently labeled molecule of formula (III) to resveratrol derivative is 0.8-1.2:1. The specific preparation process is as follows:

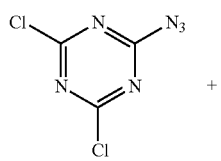

+

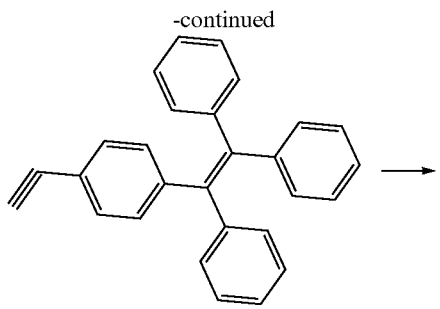

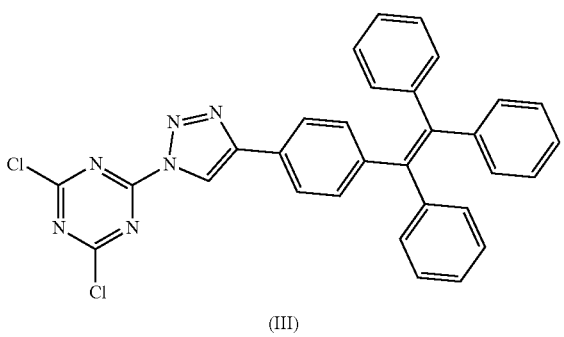

(III)

The: Mixing 0.229 g (1.2 mmol) of 2-azido-4,6-dichloro-1,3,5-triazine, 0.356 g (1 mmol) of tetraphenylacetylene, 0.025 g (0.1 mmol) of anhydrous copper sulfate, 0.198 g (1 mmol) of sodium scabate, 20 mL t-butanol, and 2 mL water, dissolving by stirring, heating to 90° C., carrying out the reaction for 10 hours. At the end of the reaction, spin-drying t-butanol, extracting the product with methylene chloride, washing and spin-drying, isolating the fluorescent marker of formula (III) by column chromatography. The product was characterized as follows:

Mp: 146~147° C.

MS (HI): m/z (%) 547.5672 [M+H]$^+$

IRvmax/cm$^{-1}$: 3440, 3070, 3022, 2960, 2918, 2849, 2194, 1733, 1621, 1513, 1456, 1410, 1306, 1260, 1076, 1051, 1018.

$^1$H NMR (500 MHz, CDCl$_3$) δ7.99 (d, J=3.7 Hz, 1H), 7.42 (d, J=8.1 Hz, 2H), 7.22~7.00 (m, 17H).

$^{13}$C NMR (126 MHz, CDCl$_3$) δ 173.18 (s), 163.48 (s), 132.47 (s), 131.65 (s), 131.54-131.14 (m), 129.39 (s), 127.91 (d, J=5.3 Hz), 127.71 (s), 127.28 (s), 127.05~126.73 (m).

The beneficial effects of the present invention are:

1, The present invention provides molecules that have a simple structure and can produce aggregation-induced luminescence, enabling light emission in the aggregation state.

2. The series of resveratrol-derivative fluorescently labeled molecules obtained by the present invention are more easily taken up by cells than fluorescent molecules of smaller molecular weight.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive. It is to be noted that various changes and modifications practiced or adopted by those skilled in the art without creative work are to be understood as being included within the scope of the present invention as defined by the appended claims.

DETAILED DESCRIPTION OF THE PREFERRED EMBODIMENTS

Figure 1:
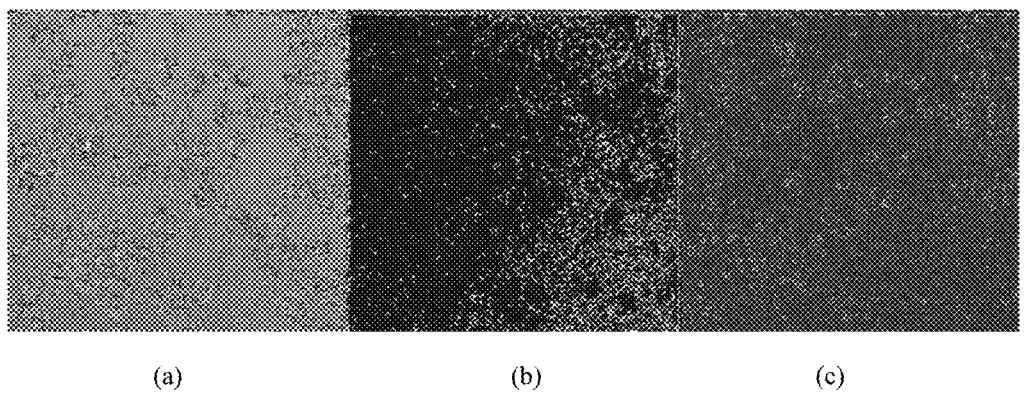
FIG. 1 is a photograph of an inverted fluorescence microscopy showing the cellular uptake of the fluorescent marker of formula III after 3 hours of incubation with cells.

The present invention will be further analyzed and described in combination with specific embodiments.

Example 1

In a 50 ml reaction vessel, 12.00 g of pterostilbene, 9.0 g of sodium hydroxide, 0.12 g of the fluorescent marker of formula III, and 20 mL of methanol were added and mixed, the temperature was controlled at 60° C., the reaction was carried out for 10 hours. After the reaction was completed, the solvent was spin-dried, and Product (I) was obtained after post-processing.

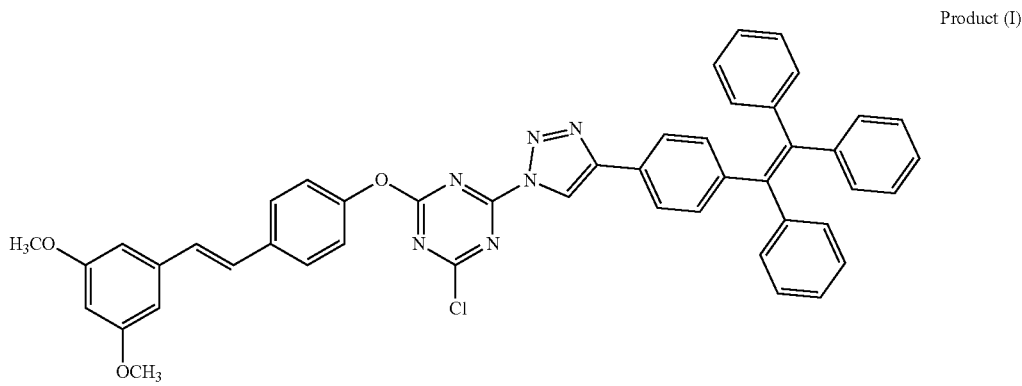 [SMILES: COc1cc(/C=C/c2ccc(Oc3nc(Cl)nc(-n4cc(-c5ccc(C(=C(c6ccccc6)c6ccccc6)c6ccccc6)cc5)nn4)n3)cc2)cc(OC)c1]

Product (I)

The Product (I) is characterized as follows:

Mp: 165-166° C.

MS (ESI): m/z (%) 767.2626 [M+H]$^+$

IRvmax/cm-1: 3445, 3072, 3020, 2961, 2916, 2849, 2190, 1752, 1623, 1588, 1532, 1465, 1420, 1365, 1295, 1120, 1051, 1023.

$^1$H NMR (500 MHz, CDCl$_3$) δ 8.58 (s, 1H), 7.68 (d, J=8.3 Hz, 2H), 7.62 (d, J=8.6 Hz, 2H), 7.26 (d, J=8.6 Hz, 2H), 7.11 (dddd, J=14.1, 10.0, 8.7, 6.6 Hz, 19H), 6.71 (d, J=2.1 Hz, 2H), 6.45 (s, 1H), 3.87 (s, 6H).

Example 2

In a 50 ml reaction vessel, 1 mol of resveratrol, 1 mol of triethylamine, 0.8 mol of the fluorescent marker of formula (III), and 5 mol of ethanol were added, the reaction was carried out under the conditions of a temperature of 20° C. for 10 hours. After the reaction was completed, the solvent was spin-dried, and the Product (II) was obtained after post-processing.

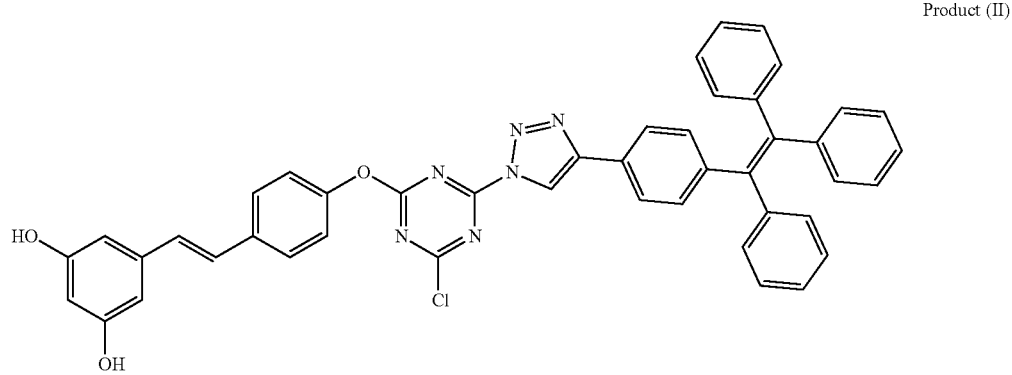 [SMILES: Oc1cc(O)cc(/C=C/c2ccc(Oc3nc(Cl)nc(-n4cc(-c5ccc(C(=C(c6ccccc6)c6ccccc6)c6ccccc6)cc5)nn4)n3)cc2)c1]

Product (II)

Example 3

In a 50 ml reaction vessel, 1 mol of resveratrol, 2.5 mol of sodium carbonate, 1.2 mol of the fluorescent marker of formula (III), and 10 mol of acetone were added, the reaction was carried out at 30° C. for 9 hours. After the reaction was completed, the solvent was spin-dried, and the product (III) was obtained after post-processing.

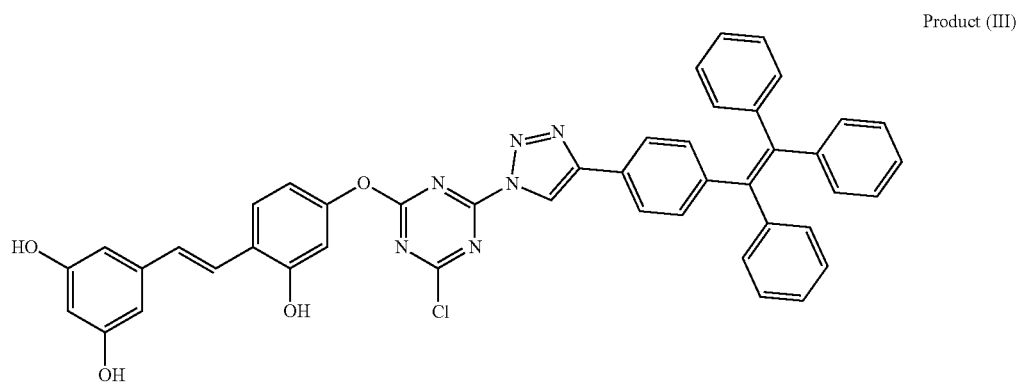 [SMILES: Oc1cc(O)cc(/C=C/c2ccc(Oc3nc(Cl)nc(-n4cc(-c5ccc(C(=C(c6ccccc6)c6ccccc6)c6ccccc6)cc5)nn4)n3)cc2O)c1]

Product (III)

Example 4

In a 50 ml reaction vessel, 1 mol of piceatannol, 1.5 mol of potassium carbonate, 1 mol of the fluorescent marker of formula (III), and 2 mol of methanol were added, the reaction was carried out at 40° C. for 7 hours. After the reaction was completed, the solvent was spin-dried, and the Product (IV) was obtained after post-processing.

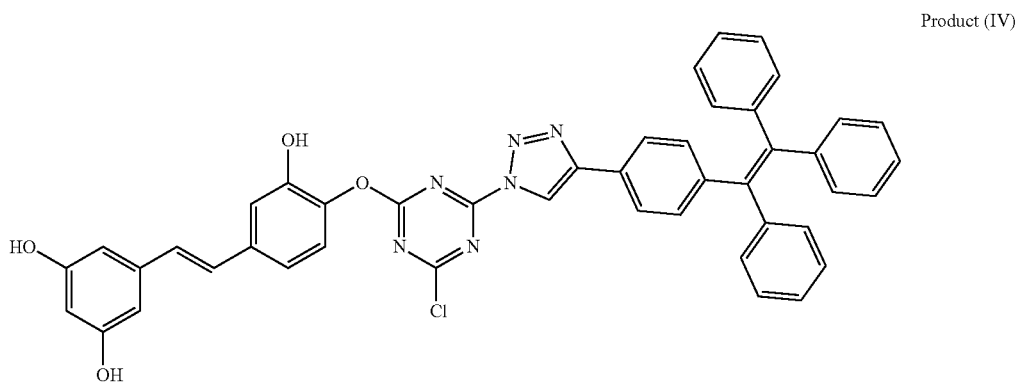 [SMILES: Oc1cc(O)cc(/C=C/c2ccc(Oc3nc(Cl)nc(-n4cc(-c5ccc(C(=C(c6ccccc6)c6ccccc6)c6ccccc6)cc5)nn4)n3)c(O)c2)c1]

Product (IV)

Example 5

In a 50 ml reaction vessel, 1 mol of combretastatin, 2 mol of sodium bicarbonate, 0.9 mol of the fluorescent marker of formula (III), and 3 mol of methanol were added, the reaction was carried out at 50° C. for 6 hours. After the reaction was completed, the solvent was spin-dried, and the Product (V) was obtained after post-processing.

Product (V)

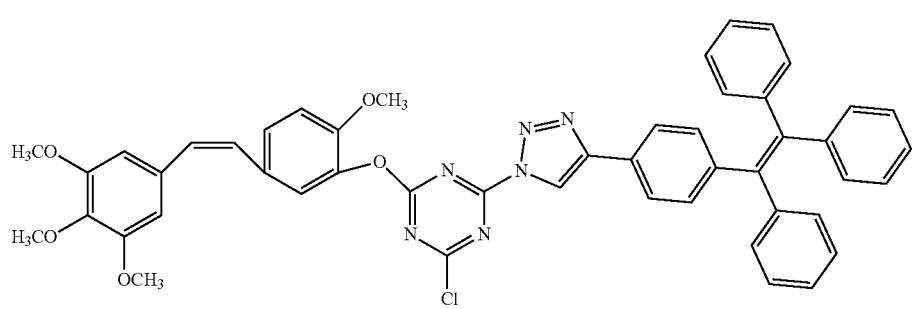

Example 6

In a 50 ml reaction vessel, 1 mol of Erianin, 2 mol of potassium bicarbonate, 1 mol of the fluorescent marker of formula (III), and 6 mol of methanol were added, the reaction was allowed to proceed at 55° C. for 4 hours. After the reaction was completed, the solvent was spin-dried, and the product was obtained after post-processing.

Product (VI)

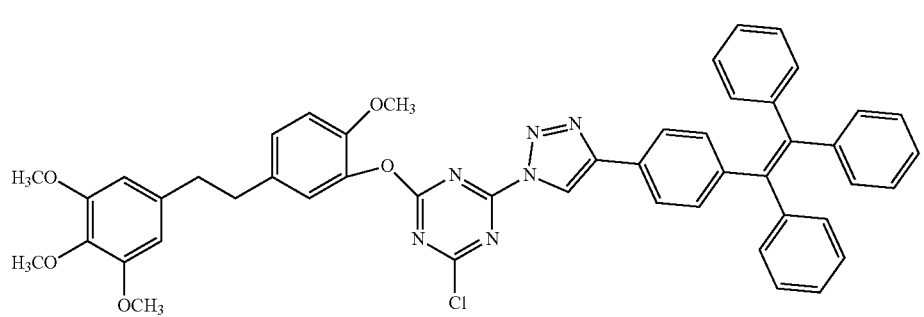

Application Examples

Cellular Uptake Experiment of the fluorescent marker of formula (III) and the Product (I), i.e., fluorescently labeled pterostilbene.

(1) Cell Inoculation

Soaking ordinary clean coverslips at 70% ethanol for 5 minutes, drying in a clean bench. Placing the coverslips in a 24-well plate, seeding cells, culturing the cells overnight to reach a cell density of 70% to 80%. Placing circular slides into each well of a 24-well plate.

Neurogenic tumor cells were suspended into DMEM culture medium containing 10% calf bovine serum. The cells were seeded onto a 24-well plate with $2\times10^4$ cells per well in a volume of 500 μL per well. The cells were cultured in a $CO_2$ incubator for 24 hours, until the cell density reaches 70% to 80%, when it is ready the uptake experiment.

(2) The fluorescent marker of formula (III) and the Product (I), i.e., fluorescently labeled pterostilbene, were formulated into a solution of 20 μg/mL with DMSO, respectively.

(3) Cellular Uptake Experiment

After incubation for 24 hours, the culture medium in the 24-well plate was aspirated off. 400 μL of serum-free DMEM culture medium was added, and the DMSO solutions of the fluorescent marker of formula (III) and the Product (I), i.e., fluorescently labeled pterostilbene, were added to 24-well plates, respectively. The 24-well plates were incubated at 37° C. in a 5% $CO_2$ incubator for 2.5 hours. Repeat the above procedure of aspirating the culture medium off the two plates, adding 4004 serum-free DMEM culture medium, adding the DMSO solution of the fluorescent marker of formula (III) and the Product I respectively, and incubate the 24-well plates at 37° C., 5% $CO_2$ in an incubator for 3 hours.

Aspirate the medium and wash three times with 200 μL of PBS. Aspirate off the PBS. Pipette 200 μl of 0.5 μg/mL Hoechst solution into each well and incubate for 6 minutes. Aspirate Hoechst solution and wash with PBS three times.

(4) Inverted Fluorescence Microscopy

FIG. 1 shows the cellular uptake of the fluorescent marker as in formula (III) after 3 hours of uptake; (a) shows the cellular uptake photo taken in white light, (b) shows the cellular uptake photo taken in blue light, and (c) is the merged rendering of (a) and (b).

Figure 2:
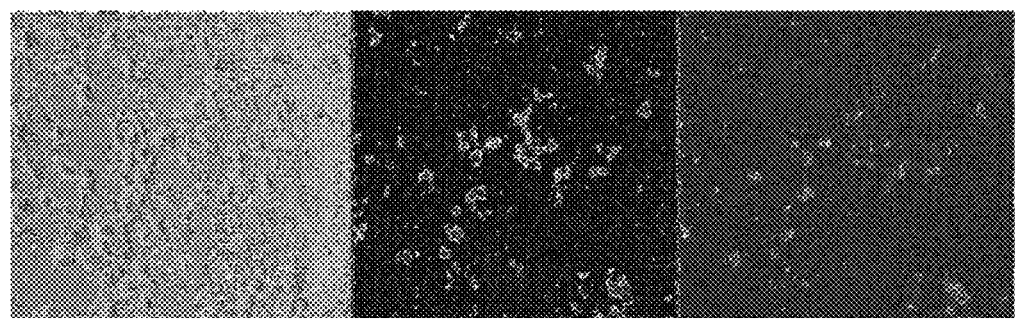
FIG. 2 a photograph of an inverted fluorescence microscopy showing the cellular uptake of the resveratrol-derivative fluorescently labeled molecules of formula (I) (the resveratrol derivative is pterostilbene) after 3 hours of incubation with cells.

FIG. 2 shows the cellular uptake of the Product (I) (the resveratrol derivative is pterostilbene) after 3 hours of uptake; (a) shows the cellular uptake photo taken in white light, (b) shows the cellular uptake photo taken in blue light, (c) is the merged rendering of (a) and (b).

The above embodiments are not intended to limit the present invention. The present invention is not limited to the above embodiments. As long as the requirements of the present invention are met, it shall fall within the protective scope of the present invention. While the invention has been particularly shown and described as referenced to the embodiments thereof, those skilled in the art will understand that the foregoing and other changes in form and detail may be made therein without departing from the spirit and scope of the invention.

2. A method for preparing the resveratrol-derivative fluorescently labeled molecules of claim 1, comprising the steps of: adding a certain amount of resveratrol derivative and solvent in a reaction vessel; adding a fluorescent marker having the formula (III) and a certain amount of alkali; carrying out the reaction at 20° C. to 60° C. for 2 to 10 hours; after the reaction is completed, spin-drying the reaction solvent; and performing post-treatment to obtain a product; wherein the reaction formula is as follows:

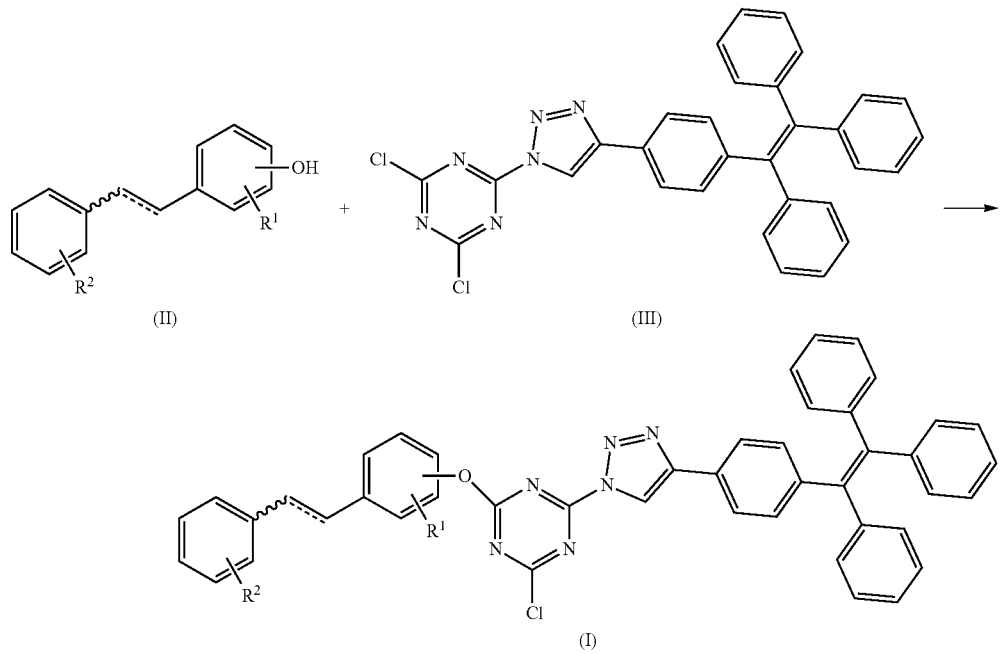

What is claimed is:

1. A series of resveratrol-derivative fluorescently labeled molecules, having the general formula (I):

(I)

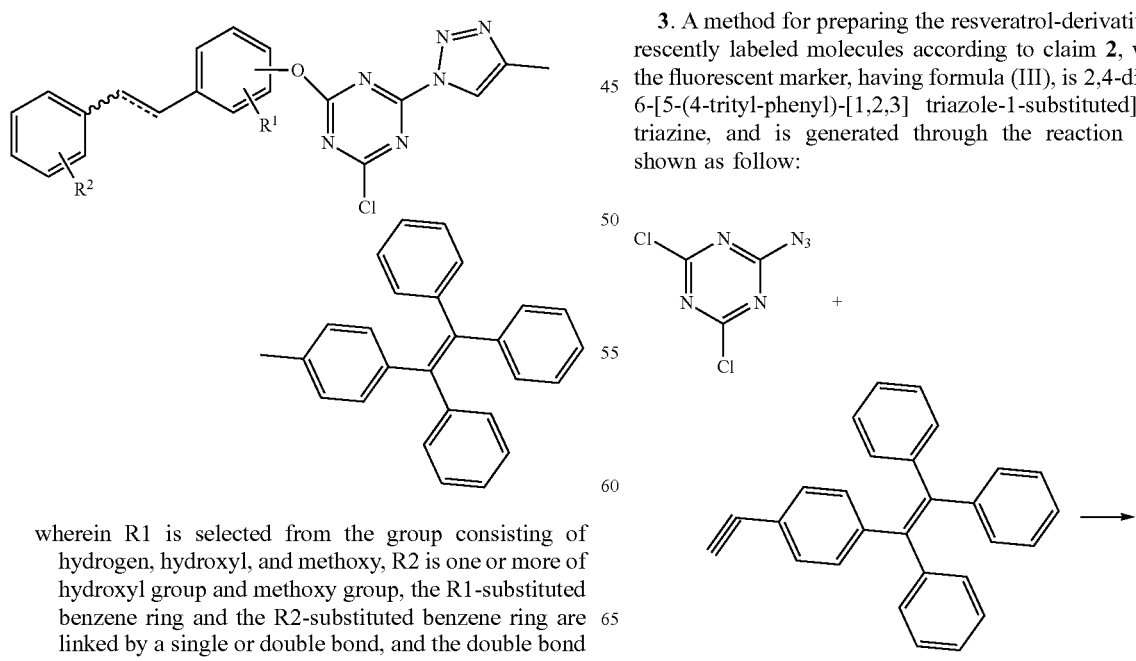

wherein R1 is selected from the group consisting of hydrogen, hydroxyl, and methoxy, R2 is one or more of hydroxyl group and methoxy group, the R1-substituted benzene ring and the R2-substituted benzene ring are linked by a single or double bond, and the double bond is cis or trans.

Wherein R1 is selected from the group consisting of hydrogen, hydroxyl, and methoxy, R2 is one or more of hydroxyl group and methoxy group, the R1-substituted benzene ring and the R2-substituted benzene ring are linked by a single or double bond, and the double bond is cis or trans.

3. A method for preparing the resveratrol-derivative fluorescently labeled molecules according to claim 2, wherein the fluorescent marker, having formula (III), is 2,4-dichloro-6-[5-(4-trityl-phenyl)-[1,2,3] triazole-1-substituted]-[1,3,5] triazine, and is generated through the reaction scheme shown as follow:

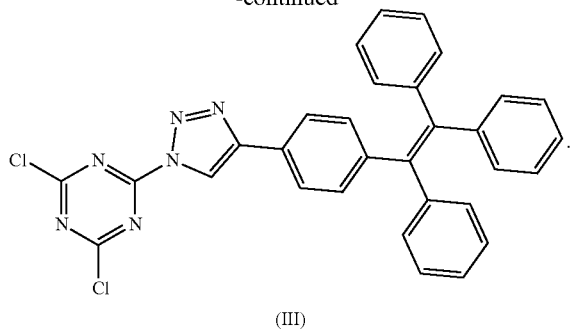

(III)

4. A method according to claim 3, wherein the fluorescent marker having formula (III) is specifically prepared by the following process:

dissolving and stirring 1.2 mmol of 2-azide-4,6-dichloro-1,3,5-triazine, 1 mmol of tetraphenylacetylene, 0.1 mmol of anhydrous copper sulfate, 1 mmol of sodium L-ascorbate, and 20 mL of t-butanol, heating to 90° C., carrying out the reaction for 10 hours, spin-drying the reaction to remove t-butanol, extracting by dichloromethane, washing and drying, filtration spin-drying, and separating the spin-dried product by column chromatography to obtain the fluorescent marker having formula (III).

5. A method according to claim 2, wherein the resveratrol derivative is selected from the group consisting resveratrol, pterostilbene, oxyresveratrol, piceatannol, combretastatin, and erianin.

6. A method according to claim 2, wherein that the solvent is selected from the group consisting of methanol, ethanol, and acetone; and the alkali is selected from the group consisting of sodium hydroxide, triethylamine, sodium carbonate, potassium carbonate, sodium bicarbonate, and potassium bicarbonate.

7. A method of claim 6, wherein the solvent is acetone, and the alkali is sodium carbonate.

8. A method according to claim 2, wherein the molar ratio of the solvent to the resveratrol derivative is 5-10:1.

9. A method according to claim 2, wherein the molar ratio of the alkali to the resveratrol derivative is 1-2.5:1.

10. The method according to claim 2, wherein the molar ratio of the fluorescent marker having formula (III) to the resveratrol derivative is 0.8-1.2:1.

* * * * *